United States Patent [19]

Boyle et al.

[11] 4,268,510

[45] May 19, 1981

[54] 1,3-BENZOXAZINE TRICHLOROMETHYL DERIVATIVES, COMPOSITIONS AND USE

[75] Inventors: Francis T. Boyle; Michael A. Taylor, both of Congleton, England

[73] Assignee: Imperial Chemical Industries Limited, London, England

[21] Appl. No.: 70,492

[22] Filed: Aug. 28, 1979

[30] Foreign Application Priority Data

Sep. 12, 1978 [GB] United Kingdom ............... 36532/78

[51] Int. Cl.³ .................... A61K 31/535; C07D 265/22
[52] U.S. Cl. ........................... 424/248.53; 424/248.54; 424/248.55; 544/92
[58] Field of Search ..................... 544/92; 424/248.53, 424/248.55, 248.54

[56] References Cited

PUBLICATIONS

Kaufmann, Chem. Abstracts, vol. 21 (1927) pp. 1866–1867.
Rana, Chem. Abstracts, vol. 37 (1943), pp. 2361–2362.
Rana et al., Chem. Abstracts, vol. 34, p. 2819.
Monti, Chem. Abstracts, vol. 34, p. 7292.
Hirwe et al., Chem. Abstracts, vol. 35 (1941) pp. 5502–5503.
Horrom et al., JACS, (1950) vol. 72, pp. 721–724.
Gilman et al., J. Org. Chem., (1976) vol. 41, pp. 737–739.

Primary Examiner—Henry R. Jiles
Assistant Examiner—R. W. Ramsuer
Attorney, Agent, or Firm—Cushman, Darby & Cushman

[57] ABSTRACT

The invention relates to novel heterocyclic trichloromethyl derivatives, particularly 2-trichloromethyl-substituted quinazoline, benzo[d]-[1,3]-oxazine and benzo[e]-[1,3]-oxazine derivatives, for example 1,2-dihydro-2-trichloromethylquinazolin-4-one. The compounds of the invention are at least as effective as prior art trichloromethyl derivatives, which reduce the production of methane during the rumen metabolism of ruminant animals, and increase the formation of propionate at the expense of acetate, and hence improve the animals' rate of growth and their efficiency of food utilization.

10 Claims, No Drawings

1,3-BENZOXAZINE TRICHLOROMETHYL DERIVATIVES, COMPOSITIONS AND USE

This invention relates to heterocyclic trichloromethyl derivatives which modify rumen metabolism in domesticated ruminant animals to reduce the production of methane, and to increase the proportion of propionic acid in the ruminal fluid at the expense of acetic acid.

It is known that various organic compounds containing a trichloromethyl group are effective in reducing methane production during the fermentation of food in the rumen. For example, chloral, chloral adducts with starch, cellulose and molasses, trichloroacetamide, and various trichloromethyl esters of lower fatty acids, such as adipic acid, are all known to have a beneficial effect on rumen metabolism when administered to ruminant animals. More recently, a variety of trichloromethyl substituted benzo[1,3]dioxin derivatives has been found to be substantially more effective than the earlier prior art simple trichloromethyl compounds. The present invention offers a further advance over the benzo[1,3]dioxins.

According to the invention there is provided a heterocyclic trichloromethyl compound of the formula:

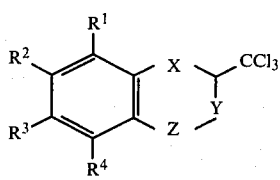

wherein either:

(a) X is an oxygen atom, Y is a radical of the formula —NR$^5$— wherein R$^5$ is a hydrogen atom, a 1–4C alkyl or alkanoyl radical or a phenyl radical which is optionally substituted by one or more halogen atoms, nitro radicals or 1–4C alkyl, alkoxy or halogenoalkyl radicals, and Z is a carbonyl radical; or (b) X is a radical of the formula —NR$^6$— wherein R$^6$ is a hydrogen atom, a 1–4C alkyl or alkanoyl radical or a phenyl radical optionally substituted as defined above for R$^5$, Y is a radical of the formula —NR$^5$— as defined above and Z is a carbonyl radical; or (c) X is a radical of the formula —NR$^6$— as defined above, Y is an oxygen atom and Z is a methylene radical, optionally substituted by a carboxy or carbamoyl radical, a 2–5C alkoxycarbonyl radical or an N-phenylcarbamoyl radical which is optionally substituted by halogen atoms, nitro radicals or 1–4C alkyl, alkoxy or halogenoalkyl radicals;

and R$^1$, R$^2$, R$^3$ and R$^4$, which may be the same or different, are each a hydrogen or halogen atom, a cyano, formyl, hydroxy, hydroxyiminomethyl, nitro or sulfo radical, a carboxy radical or an alkali metal, alkaline earth metal or ammonium salt thereof, or a radical of the formula R$^7$, OR$^7$, OCH$_2$R$^{10}$, CO.OR$^7$, O.COR$^7$, O.COR$^{10}$, CONR$^8$R$^9$, NR$^8$R$^9$, NR$^8$.COR$^9$, NH.SO$_2$R$^{10}$, NH.CH$_2$R$^{10}$, SO$_2$.NR$^8$R$^9$ or SO$_2$.OR$^7$, wherein R$^7$ is a 1–4C alkyl radical, R$^8$ and R$^9$, which may be the same or different, are each a hydrogen atom or a 1–4C alkyl radical and R$^{10}$ is a phenyl radical optionally substituted as defined above for R$^5$; but excluding those compounds wherein Z is a carbonyl radical and:

(i) X is an oxygen atom or an imino radical, Y is an imino radical and R$^1$, R$^2$, R$^3$ and R$^4$ are all hydrogen atoms; or (ii) X is an oxygen atom, Y is an imino radical and either R$^2$ and R$^4$ are chlorine atoms and R$^1$ and R$^3$ are hydrogen atoms, or R$^3$ is an acetamido radical and R$^1$, R$^2$ and R$^4$ are hydrogen atoms; or (iii) X is an oxygen atom, Y is an acetylimino radical, R$^3$ is an acetamido radical and R$^1$, R$^2$ and R$^4$ are all hydrogen atoms.

A suitable value for any of R$^1$, R$^2$, R$^3$ and R$^4$ when it is a halogen atom or for a halogen substituent in a phenyl radical R$^5$, R$^6$ or R$^{10}$ is, for example, a chlorine, bromine or iodine atom.

A particular value for any of R$^1$, R$^2$, R$^3$ and R$^4$, when it is a radical of the formula R$^7$; for R$^5$ or R$^6$ when either is a 1–4C alkyl radical; for a 1–4C alkyl substituent in R$^5$, R$^6$ or R$^{10}$ when either is a 1–4C alkyl-substituted phenyl radical; or for a 1–4C alkyl substituent in the phenyl ring of Z when it is an N-phenylcarbamoyl-substituted methylene radical; is a methyl, ethyl, propyl, isopropyl, butyl, isobutyl, s-butyl or t-butyl radical.

A particular value for any of R$^1$, R$^2$, R$^3$ and R$^4$ when it is a radical of the formula OR$^7$; for a 1–4C alkoxy substituent in any of R$^5$, R$^6$ and R$^{10}$ when it is a 1–4C alkoxy-substituted phenyl radical; or for a 1–4C alkoxy substituent in the phenyl ring of Z when it is an N-phenylcarbamoyl substituted methylene radical; is a methoxy, ethoxy, propoxy, isopropoxy, butoxy, isobutoxy, s-butoxy or t-butoxy radical.

A particular value for any of R$^1$, R$^2$, R$^3$ and R$^4$ when it is a radical of the formula CO.OR$^7$ or for a 2–5C alkoxycarbonyl substituent in Z when it is an alkoxycarbonyl-substituted methylene radical, is a methoxycarbonyl, ethoxycarbonyl, propoxycarbonyl, isopropoxycarbonyl, butoxycarbonyl, isobutoxycarbonyl, s-butoxycarbonyl or t-butoxycarbonyl radical.

A particular value for any of R$^1$, R$^2$, R$^3$ and R$^4$ when it is a radical of the formula O.COR$^7$ is, for example, an acetoxy, propionyloxy, butyryloxy or isobutyryloxy radical.

A particular value for any of R$^1$, R$^2$, R$^3$ and R$^4$ when it is a radical of the formula O.CH$_2$R$^{10}$ is, for example, a benzyloxy, chlorobenzyloxy or methylbenzyloxy radical.

A particular value for any of R$^1$, R$^2$, R$^3$ and R$^4$ when it is a radical of the formula O.COR$^{10}$ is, for example, a benzoyloxy, chlorobenzoyloxy or methylbenzoyloxy radical.

A particular value for a 1–4C halogenoalkyl substituent in any of R$^5$, R$^6$ and R$^{10}$ when it is a halogenoalkyl-substituted phenyl radical, or in the phenyl ring of Z when it is an N-phenylcarbamoyl-substituted methylene radical, is for example a trichloromethyl, trifluoromethyl, 2,2,2-trichloroethyl, 3,3,3-trichloropropyl or 2,2,3,3,3-pentachloropropyl radical.

A particular value for R$^5$ or R$^6$ when either is a 1–4C alkanoyl radical is a formyl, acetyl, propionyl, butyryl or isobutyryl radical.

A particular value for any of R$^1$, R$^2$, R$^3$ and R$^4$ when it is a radical of the formula CO.NR$^8$R$^9$ is, for example, a carbamoyl, methylcarbamoyl, dimethylcarbamoyl, ethylcarbamoyl, diethylcarbamoyl, propylcarbamoyl, dipropylcarbamoyl, isopropylcarbamoyl, butylcarbamoyl, isobutylcarbamoyl, s-butylcarbamoyl, t-butylcarbamoyl or ethylmethylcarbamoyl radical.

A particular value for any of $R^1$, $R^2$, $R^3$ and $R^4$ when it is a radical of the formula $NR^8R^9$ is, for example, an amino, methylamino, dimethylamino, ethylamino, diethylamino, propylamino, dipropylamino, isopropylamino, butylamino, isobutylamino, s-butylamino, t-butylamino or ethylmethylamino radical.

A particular value for any of $R^1$, $R^2$, $R^3$ and $R^4$ when it is a radical of the formula $NR^8.COR^9$ is, for example, an acetamido, N-methylacetamido, N-ethylacetamido, N-propylacetamido, N-isopropylacetamido, N-butylacetamido, propionamido, N-methylpropionamido, N-ethylpropionamido, butyramido, N-methylbutyramido, N-ethylbutyramido, 2-methylpropionamido or N,2-dimethylpropionamido radical.

A particular value for any of $R^1$, $R^2$, $R^3$ and $R^4$ when it is a radical of the formula $SO_2.NR^8R^9$ is, for example, a sulfamoyl, methylsulfamoyl, dimethylsulfamoyl, ethylsulfamoyl, diethylsulfamoyl, propylsulfamoyl, dipropylsulfamoyl, isopropylsulfamoyl, butylsulfamoyl, isobutylsulfamoyl, s-butylsulfamoyl, t-butylsulfamoyl or ethylmethylsulfamoyl radical.

A particular value for any of $R^1$, $R^2$, $R^3$ and $R^4$ when it is a radical of the formula $SO_2.OR^7$ is a methoxysulfonyl, ethoxysulfonyl, propoxysulfonyl, isopropoxysulfonyl, butoxysulfonyl, isobutoxysulfonyl, s-butoxysulphonyl or t-butoxysulfonyl radical.

Particularly valuable compounds of the invention are 3,4-dihydro-6-hydroxy-2-trichloromethyl-2$\underline{H}$-benzo[e]-[1,3]-oxazin-4-one, 3,4-dihydro-4-oxo-2-trichloromethyl-2$\underline{H}$-benzo[e]-[1,3]-oxazine-6-carboxylic acid, 6-acetoxy-3,4-dihydro-2-trichloromethyl-2$\underline{H}$-benzo[e]-[1,3]-oxazine-4-one, 6-acetoxy-1,2-dihydro-2-trichloromethyl-4$\underline{H}$-benzo[d]-[1,3]-oxazine, 1,2-dihydro-2-trichloromethyl-4$\underline{H}$-benzo[d]-[1,3]-oxazine-4-carboxylic acid and ethyl 1,2-dihydro-2-trichloromethyl-4$\underline{H}$-benzo[d]-[1,3]-oxazine-4-carboxylate.

According to a further feature of the invention there is provided a process for the manufacture of a heterocyclic trichloromethyl compound of the formula I, which comprises the reaction of a compound of the formula:

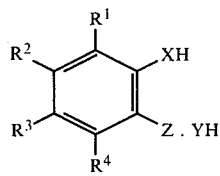

II wherein $R^1$, $R^2$, $R^3$, $R^4$, X, Y and Z have the meanings stated above, with chloral optionally in the presence of a solvent and, either simultaneously or subsequently, with an acid, whereafter, if desired, particular substituents $R^1$, $R^2$, $R^3$ and $R^4$ and, if present in X or Y, $R^5$ and $R^6$, may be transformed to other such substituents, as defined above, by conventional methods in actual use or known in the literature of organic chemistry.

A suitable acid for use in the above process is, for example, sulphuric acid or hydrochloric acid.

When a solvent is used in the above process, bis(2-methoxyethyl)ether, (dimethyl diethyleneglycol, dimethyl digol, diglyme) is preferred. Other solvents tend to result in partial loss of chlorine from the trichloromethyl group of the product.

Examples of optional transformations on the primary products of the above process are:

(a) alkylation of a hydroxy-substituted product to give an alkoxy-substituted product, of a carbamoyl-substituted product to give a mono- or di-N-alkylcarbamoyl-substituted product, of an alkanoylamino-substituted product to give an N-alkyl-alkanoylamino-substituted product, of a sulfamoyl-substituted product to give a mono- or di-N-alkylsulfamoyl-substituted product, or of a ring NH product to give a ring N-alkyl product;

(b) alkanoylation of a hydroxy-substituted product to give an alkanoyloxy-substituted product, of an amino-substituted product to give an alkanoylamino-substituted product, or of a ring NH product to give a ring N-alkanoyl product;

(c) esterification of a carboxy-substituted product to give an alkoxycarbonyl-substituted, product, or of a sulfo-substituted product to give an alkoxysulfonyl-substituted product;

(d) amination of a carboxy-substituted or alkoxycarbonyl-substituted product to give a carbamoyl- or a mono- or di-N-alkylcarbamoyl-substituted product, or of a sulfo-substituted or alkoxysulfonyl-substituted product to give a sulfamoyl- or a mono- or di-N-alkylsulfamoyl-substituted product;

(e) hydrolysis of an alkanoyloxy-substituted product to give a hydroxy-substituted product, of a cyano-, alkoxycarbonyl-, carbamoyl- or mono- or di-N-alkylcarbamoyl-substituted product to give a carboxy-substituted product, or of an alkoxysulfonyl-, sulfamoyl- or mono- or di-N-alkylsulfamoyl-substituted product to give a sulfo-substituted product;

(f) de-alkylation of an alkoxy-substituted product to give a hydroxy-substituted product;

(g) reduction of a nitro-substituted product to give an amino-substituted product; or of a benzylideneamino-substituted product to give a benzylamino-substituted product;

(h) oximination of a formyl-substituted product to give a hydroxyiminomethyl-substituted product;

(i) sulphonation of a product unsubstituted in the aromatic ring to give a sulfo-substituted product.

As stated above, the heterocyclic trichloromethyl derivatives of the formula I reduce the production of methane, and increase the proportion of propionic acid in the ruminal fluid, in ruminant animals and are therefore valuable for the more efficient management of domesticated ruminant animals.

According to a further feature of the invention, therefore, there is provided a method for reducing ruminal methane production and/or for increasing the proportion of propionic acid in the ruminal fluid, in domesticated ruminant animals, which comprises orally administering to the animals a heterocyclic trichloromethyl compound of the formula I wherein $R^1$, $R^2$, $R^3$, $R^4$, X, Y and Z have any of the meanings stated above.

In the method of the invention, the compound of the formula I is preferably orally administered to the animals as a supplement to their normal diet, that is to say, in admixture with an ordinary solid foodstuff, in feedblocks or salt-licks, dissolved in the drinking water or, for young animals such as weaned lambs or calves, dissolved in whole milk or skim milk. The compound of the formula I is incorporated into food, feedblocks, salt-licks, drinking water, whole milk or skim milk to such an extent that each treated animals will ingest from 0.1 mg./kg. body weight to 30 mg./kg. body weight per day, preferably from 0.1 mg./kg. to 10 mg./kg. per day, of the compound of the formula I.

The compound of the formula I may alternatively be orally administered to animals in the form of a slowrelease, intra-ruminal pellett or bolus, such that the animal will absorb a similar quantity per day of the compound of the formula I.

The animals may receive a compound of the formula I for substantially the whole of their growing period, or for only a part of their growing period, for example the early part and/or the period leading up to slaughter. At optimum methane-inhibiting inclusion levels, no indication of any toxic effect due to the compound of the formula I is observed.

According to a further feature of the invention, there is provided a composition which comprises a heterocyclic trichloromethyl compound of the formula I wherein $R^1$, $R^2$, $R^3$, $R^4$, X, Y and Z have any of the meanings stated above together with a solid or liquid edible, non-toxic diluent or carrier.

A suitable liquid diluent or carrier is, for example, drinking water, whole milk or skim milk.

A suitable solid, edible, non-toxic diluent or carrier may be, for example, a conventional nutritionally balanced ruminant feedstuff, for example a typical cattle or sheep diet consisting of cereal products, such as barley meal, maize meal or wheet feed, nut and seed products, such as decorticated ground nut cake or cotton seed cake, or extracted cotton seed cake, together with minor amounts of, for example, feather meal, seaweed meal, bone meal, bone flour, chalk, salt, urea, molasses, vitamins and trace minerals; or it may be an inert solid diluent or carrier of no nutritional value, for example kaolin, talc, calcium carbonate, fuller's earth, attapulgus clay, ground oyster shells or ground limestone; or it may be starch or lactose.

The composition of the invention may take the form of a supplemented feedstuff for direct feeding to animals, in which case it will contain from 3 ppm to 3000 ppm of a compound of the formula I in admixture with a conventional ruminant feedstuff; or it may take the form of a concentrated premix for dilution with a conventional ruminant feedstuff to produce a supplemented feedstuff suitable for direct feeding, and such a premix will contain from 0.3% w/w to 50% w/w of a compound of the formula I in admixture with either a conventional, nutritionally balanced ruminant feedstuff, an inert solid diluent of no nutritional value, for example ground limestone, or starch or lactose.

According to a further feature of the invention there is provided a process for the manufacture of a solid composition of the invention which comprises uniformly mixing a heterocyclic trichloromethyl compound of the formula I with a solid, edible, non-toxic diluent or carrier.

The compound of the formula I is preferably serially diluted with the diluent or carrier in two or more successive stages, to ensure even mixing.

The invention is illustrated, but not limited, by the following Examples:

EXAMPLE 1

Anthranilamide hydrochloride (63.5 g.) was heated under reflux with anhydrous chloral (650 ml.) for three hours. The resulting solution was evaporated to dryness, and the residue was triturated with toluene (700 ml.) to give a yellow product containing one mole of chloral. This was removed by boiling the product with methanol (2 l.) for 15 minutes, cooling the solution and filtering. The filtrate was concentrated to half its volume, and allowed to cool, to produce 1,2-dihydro-2-trichloromethylquinazolin-4-one, m.p. 201°–202° C.

The process described above was repeated, using the appropriate substituted anthranilamide as starting material, to give the following products:

| $R^3$ | $R^5$ | $R^6$ | M.p. (°C.) |
|---|---|---|---|
| H | H | $CH_3$ | 192–194 |
| H | $CH_3$ | H | 158–160 |
| H | $CH_3$ | $CH_3$ | 188–190 |
| Cl | H | H | 224–225 |

EXAMPLE 2

5-Nitroanthranilamide (6.5 g.) and anhydrous chloral (65 ml.) were stirred together at ambient temperature, until thin layer chromatography indicated that all the 5-nitroanthranilamide had disappeared (6 days). The excess of chloral was distilled off, and the resulting syrup was heated with concentrated sulphuric acid (125 ml.) on a steam bath for 10 minutes. The reaction mixture was cooled and poured into ice/water (1 kg.), and the solid product which was precipitated was filtered off, washed with water (3×200 ml.) and crystallised from ethanol (450 ml.) to give 1,2-dihydro-6-nitro-2-trichloromethylquinazolin-4-one, m.p. 278°–280° C.

EXAMPLE 3

Salicylamide (40.0 g.) and anhydrous chloral (400 ml.) were heated together on a steam-bath for 3 hours, the reaction mixture was cooled, and the excess of chloral was evaporated under reduced pressure. The syrupy product was mixed with concentrated sulphuric acid (500 ml.) and heated on a steam-bath for 1 hour. The mixture was cooled and poured into crushed ice (3 kg.), and the precipitated solid was filtered off, triturated with diethyl ether (300 ml.) and filtered again. The solid product was stirred with water (1 l.), filtered, washed well with water, dried and crystallised from ethanol (400 ml.) to yield 3,4-dihydro-2-trichloromethyl-2H-benzo[e]-[1,3]-oxazin-4-one, m.p. 175°–177° C.

The process described above was repeated, using the appropriate substituted salicylamide as starting material, to give the following compounds:

| $R^3$ | M.p. (°C.) |
|---|---|
| Br | 218–220 |
| HO | 238–240 (decomposition) |
| $CH_3$ | 199–200 |
| $NO_2$ | 201–203 |
| COOH | 301–303 (decomposition) |

EXAMPLE 4

A suspension of 3,4-dihydro-6-hydroxy-2-trichloromethyl-2H-benzo[e]-[1,3]-oxazin-4-one (prepared as described in Example 3—2.5 g.) in ethanol (125 ml.) was stirred, ethanolic sodium hydroxide (32 ml. of a 0.36 M solution) was added, and the mixture was stirred for 30 minutes. Iodomethane (1.5 ml.) was added, and the solution was heated on a steam-bath for 1 hour. The solvent was evaporated under reduced pressure, and the residue was dissolved in a mixture of diethyl ether (100 ml.) and N sodium hydroxide solution (50 ml.). The ether layer was separated, the aqueous layer was re-extracted with ether (100 ml.), and the ether extracts were combined and dried. The solvent was evaporated, and the sticky residue was stirred for 15 minutes with petroleum ether (b.p. 60°–80°, 100 ml.), then filtered and washed with more petroleum ether to yield 3,4-dihydro-6-methoxy-2-trichloromethyl-2H-benzo[e]-[1,3]-oxazin-4-one, m.p. 162°–165° C.

The process described above was repeated, using benzyl bromide or n-butyl iodide in place of iodomethane, to give respectively:
  (a) 6-benzyloxy-3,4-dihydro-2-trichloromethyl-2H-benzo[e]-[1,3]-oxazin-4-one, m.p. 228°–230° C.; and
  (b) 6-butyloxy-3,4-dihydro-2-trichloromethyl-2H-benzo[e]-[1,3]-oxazin-4-one, m.p. 140°–141° C.

The petroleum ether filtrate and washings from the process described above were combined, the solvent was evaporated, and the residue was triturated with cyclohexane to yield 3,4-dihydro-6-methoxy-3-methyl-2-trichloromethyl-2H-benzo[e]-[1,3]-oxazin-4-one, m.p. 107°–110° C.

EXAMPLE 5

3,4-Dihydro-6-hydroxy-2-trichloromethyl-2H-benzo[e]-[1,3]-oxazin-4-one (prepared as described in Example 3—5.0 g.) and acetic anhydride (250 ml.) were stirred for 40 hours at room temperature, the mixture was filtered, and the solid product was washed with acetic anhydride, then diethyl ether, to give 6-acetoxy-3,4-dihydro-2-trichloromethyl-2H-benzo[e]-[1,3]-oxazin-4-one, m.p. 201°–203° C.

The process described above was repeated, using propionic anhydride or p-chlorobenzoyl chloride in place of acetic anhydride, to give respectively:
  (a) 3,4-dihydro-6-propionyloxy-2-trichloromethyl-2H-benzo[e]-[1,3]-oxazin-4-one, m.p. 183°–185° C.; and
  (b) 6-p-chlorobenzoyloxy-3,4-dihydro-2-trichloromethyl-2H-benzo[e]-[1,3]-oxazin-4-one, m.p. 220°–222° C.

EXAMPLE 6

3,4-Dihydro-6-hydroxy-2-trichloromethyl-2H-benzo[e]-[1,3]-oxazin-4-one (prepared as described in Example 3—10.0 g.) was stirred with acetic anhydride (200 ml.) on a steam-bath for 2 hours. The reaction mixture was cooled and poured into water (1 l.), stirred for 3 hours and filtered. The solid product was washed throughly with water and dried to give 6-acetoxy-3-acetyl-3,4-dihydro-2-trichloromethyl-2H-benzo[e]-[1,3]-oxazin-4-one, m.p. 138°–140° C.

The process described above was repeated, using propionic anhydride instead of acetic anhydride, to give 3,4-dihydro-3-propionyl-6-propionyloxy-2-trichloromethyl-2H-benzo[e]-[1,3]-oxazin-4-one, m.p. 92°–94° C.

EXAMPLE 7

3,4-Dihydro-2-trichloromethyl-2H-benzo[e]-[1,3]-oxazin-4-one (prepared as described in Example 3—4.0 g.) was stirred with acetic anhydride (40 ml.) on a steam-bath for 10 hours. The reaction mixture was cooled to room temperature, poured into water (400 ml.) and stirred for 3 hours, and the oil which separated was extracted into diethyl ether. The extract was dried and the solvent was evaporated to leave an oil, which was purified by column chromatography on "Kieselgel 60" (trade mark) silica, and the column was eluted with 10% v/v ethyl acetate in toluene. 25 Ml. fractions were collected, fractions 1–7 were combined, and the solvent was evaporated to give 3-acetyl-3,4-dihydro-2-trichloromethyl-2H-benzo[e]-[1,3]-oxazin-4-one as an oil. The n.m.r. spectrum in hexadeuterio-dimethylsulphoxide showed the following characteristic peaks (δ values):

2.6, 3H, singlet, —COC$H_3$
7.1, 1H, singlet, C-2 proton
7.15, 1H, double doublet (J=8 and 2 Hz.), C-8 proton
7.21, 1H, triplet of doublets (J=8 and 2 Hz.), C-7 proton
7.7, 1H, triplet of doublets (J=8 and 2 Hz.), C-6 proton
7.9, 1H, double doublet (J=8 and 2 Hz.), C-5 proton

EXAMPLE 8

Dimethylformamide (20 ml.) and thionyl chloride (5 ml.) were stirred together, 3,4-dihydro-2-trichloromethyl-2H-benzo[e]-[1,3]-oxazin-4-one (2.0 g.) was added in small portions over 15 minutes, and the mixture was stirred at ambient temperature for 48 hours. The reaction mixture was added to water (100 ml.), stirred for 1 hour and filtered. The solid product was dissolved in toluene, and purified by column chromatography on "Kieselgel"-60 (trade mark), eluting with a mixture of 5% by volume of ethyl acetate in toluene. The solvent was evaporated, and the product was crystallised from petroleum ether (b.p. 60°–80° C.) to give 3-formyl-3,4-dihydro-2-trichloromethyl-2H-benzo[e]-[1,3]-oxazin-4-one, m.p. 114° C.

EXAMPLE 9

A suspension of powdered 3,4-dihydro-4-oxo-2-trichloromethyl-2H-benzo[e]-[1,3]-oxazine-6-carbonyl chloride (5.0 g.) in n-butanol (100 ml.) was heated on a steam bath for 30 minutes. The solution was cooled to ambient temperature, and the solvent was evaporated under reduced pressure. The sticky solid residue was triturated with petroleum ether (b.p. 60°–80° C.), filtered, washed with petroleum ether and crystallised from n-butanol to give butyl 3,4-dihydro-4-oxo-2-trichloromethyl-2H-benzo[e]-[1,3]-oxazine-6-carboxylate, m.p. 134°–136° C.

The 3,4-dihydro-4-oxo-2-trichloromethyl-2H-benzo[e]-[1,3]oxazine-6-carbonyl chloride used as the starting material in the above process may be obtained as follows:

A suspension of 3,4-dihydro-4-oxo-2-trichloromethyl-2H-benzo[e]-[1,3]-oxazine-6-carboxylic acid (21 g.) in thionyl chloride (400 ml.) was stirred and heated under reflux for 4 hours.

The solution was cooled and the excess of thionyl chloride was evaporated under reduced pressure below 80° C. The solid product was dried in air for 30 minutes, then stored in a vacuum desiccator.

The process described above was repeated using methanol in place of n-butanol to give methyl 3,4-dihydro-4-oxo-2-trichloromethyl-2H-benzo[e]-[1,3]-oxazine-6-carboxylate, m.p. 218°–220° C.

EXAMPLE 10

Powdered 3,4-dihydro-4-oxo-2-trichloromethyl-2H-benzo[e]-[1,3]-oxazine-6-carbonyl chloride (5.0 g.) was stirred while a solution of n-propylamine (5 ml) in methanol (100 ml.) was added, the resulting solution was stirred for 30 minutes, and the solvent was evaporated under reduced pressure to give a sticky solid residue. The residue was triturated with water and the resulting suspension was stirred for 30 minutes and filtered. The solid product was washed with water, dried and crystallised from ethanol to give 3,4-dihydro-4-oxo-N-propyl-2-trichloromethyl-2H-benzo[e]-[1,3]-oxazine-6-carboxamide, m.p. 228°–230° C.

The process described above was repeated, using ammonia or diethylamine in place of n-propylamine, to give respectively:

3,4-dihydro-4-oxo-2-trichloromethyl-2H-benzo[e]-[1,3]-oxazine-6-carboxamide, m.p. 263°–265° C. (with decomposition); and 3,4-dihydro-N,N-diethyl-4-oxo-2-trichloromethyl-2H-benzo[e]-[1,3]-oxazine-6-carboxamide, m.p. 162°–164° C.

EXAMPLE 11

A solution of o-aminobenzyl alcohol (2.4 g.) in toluene (5 ml.) was stirred at ambient temperature while anhydrous chloral (2.0 ml.) was added dropwise. The mixture was stirred for 30 minutes, and evaporated to dryness to yield an oil, which was crystallised from aqueous ethanol to give 1,2-dihydro-2-trichloromethyl-4H-benzo[d]-[1,3]-oxazine, m.p. 90°–92° C.

The process described above was repeated, using the appropriate substituted o-aminobenzyl alcohol as starting material, to give the following analogous products:

(a) 1,2-dihydro-6-methyl-2-trichloromethyl-4H-benzo[d]-[1,3]oxazine, m.p. 102° C.

(b) 1,2-dihydro-6-nitro-2-trichloromethyl-4H-benzo[d]-[1,3]oxazine, m.p. 144° C.

The 2-amino-5-nitrobenzyl alcohol used as the starting material in the preparation of this compound may be obtained as follows:

A suspension of 2-amino-5-nitrobenzaldehyde (6.0 g.) in ethanol (250 ml.) was stirred at ambient temperature while sodium borohydride (1.6 g.) was added in small portions, and the reaction mixture was stirred for 1 hour. The reaction mixture was made acid with 2 N hydrochloric acid to destroy the excess of sodium borohydride, and then basified to pH 8 to 9 with solid sodium carbonate and extracted with diethyl ether (3×200 ml.). The extracts were combined and dried, the solvent was evaporated and the residue was crystallised from water (about 200 ml.) to give the required 2-amino-5-nitrobenzyl alcohol, m.p. 141°–142° C.;

(c) 1,2-dihydro-6-iodo-trichloromethyl-4H-benzo[d]-[1,3]-oxazine, m.p. 113° C.;

(d) 1,2-dihydro-6-methoxy-2-trichloromethyl-4H-benzo[d]-[1,3]-oxazine, m.p. 112° C.

The 2-amino-5-methoxybenzyl alcohol used as the starting material in the preparation of this compound may be obtained as follows:

A solution of 5-methoxy-2-nitrobenzaldehyde (2.3 g.) in ethanol (100 ml.) was stirred at ambient temperature, sodium borohydride (0.6 g.) was added and stirring was continued for 2 hours. Water (100 ml.) was added, and the solution was acidified with 2 N hydrochloric acid and extracted with ether (3×100 ml.). The extracts were combined and dried and the solvent was evaporated to give 5-methoxy-2-nitrobenzyl alcohol.

This alcohol (2.1 g.) was dissolved in ethanol (100 ml.), Adams' platinum oxide catalyst was added, and the mixture was shaken with hydrogen at ambient temperature and pressure until 950 ml. of hydrogen had been absorbed (theoretical quantity=900 ml.). The hydrogenated mixture was filtered through "Supercel" (trademark) kieselguhr, and the solvent was evaporated to give 2-amino-5-methoxybenzyl alcohol as a brown solid;

(e) 1,2-dihydro-2-trichloromethyl-4H-benzo[d]-[1,3]-oxazine-6-carbonitrile, m.p. 109° C.

The 4-amino-3-hydroxymethylbenzonitrile used as the starting material in the preparation of this compound may be obtained as follows:

2-Amino-5-iodobenzyl alcohol (12 g.) and cuprous cyanide (5.4 g.) in dry dimethylformamide (10 ml.) were heated on a steam-bath for 30 hours, then cooled to ambient temperature and poured into a solution of ferric chloride (10 g.) in water (100 ml.). This mixture was exhaustively extracted with ether (14×60 ml.), the extracts were combined and dried, and the solvent was evaporated. The residue was chromatographed on a column of "Merck 7734" silica, and elution with ether yielded the required 4-amino-3-hydroxymethylbenzonitrile as a buff-coloured solid.

EXAMPLE 12

The ability of the heterocyclic trichloromethyl compounds of the invention to inhibit the production of methane from ruminal fluid may conveniently be demonstrated by an in vitro assay, as follows:

Rumen fluid is collected on a regular routine basis from two steers, which are fed on the same hay-plus-concentrate diet. Sampling time is standardised as far as possible, and the fluid from the two animals is pooled on a 50/50 basis. Large particulate matter is removed by filtering the pooled fluid through four layers of muslin cloth. The filtrate is then diluted in the ratio of one volume of filtrate to three volumes of an artificial rumen fluid (prepared as described by G. L. Bales et al., Journal of Dairy Science, 1976, volume 59, page 1850, but omitting acetic acid), and the pH of the mixture is adjusted to 6.9–7.0 with saturated aqueous sodium carbonate solution. Aliquots (50 ml.) of this mixture are dispensed into 100 ml. conical flasks containing dried ground hay (0.5 g.), and each flask is used to test a test compound at a particular concentration.

The test compound is added to the conical flask as a solution in ethanol, the flask is flushed with carbon dioxide gas, stoppered with a suba-seal, and incubated at 39° C. for 15–16 hours. After one hour, a narrow bore needle is inserted through the suba-seal to relieve the gas pressure, and the needle is withdrawn 30 minutes before the incubation is ended. Fermentation is then stopped by placing the flask in ice, and after 15 minutes cooling, the gas over the liquid is analysed for methane by gas chromatography, and the concentration of the test compound required to produce a 50% reduction in methane production ($ED_{50}$ in $\mu g./ml.$) is calculated.

The following results were obtained:

| | | | |
|---|---|---|---|
| | | | (structure: benzene with R³, N-R⁶ attached to CH-CCl₃, and C(=O)-N-R⁵) |
| R³ | R⁵ | R⁶ | ED₅₀ |
| H | H | H | 0.3 |
| H | H | CH₃ | 0.3 |
| H | CH₃ | H | 1.0 |
| H | CH₃ | CH₃ | 1.0 |
| NO₂ | H | H | 3.0 |
| Cl | H | H | 0.3 |

| | | |
|---|---|---|
| | | (structure: benzene with R³, O-CH(CCl₃), and C(=O)-N-R⁵) |
| R³ | R⁵ | ED₅₀ |
| H | H | 0.5 |
| Br | H | 0.5 |
| HO | H | 0.5 |
| CH₃O | H | 0.5 |
| CH₃CO.O | H | 0.3 |
| C₆H₅.CH₂O | H | 10.0 |
| CH₃(CH₂)₃O | H | 3.0 |
| C₂H₅CO.O | H | 0.3 |
| CH₃ | H | 1.0 |
| NO₂ | H | 1.0 |
| HO.CO | H | 0.3 |
| p-Cl.C₆H₄CO.O | H | 1.0 |
| CH₃(CH₂)₂NH.CO | H | 0.3 |
| NH₂CO | H | 0.3 |
| CH₃(CH₂)₃O.CO | H | 1.0 |
| (C₂H₅)₂N.CO | H | 0.3 |
| CH₃O.CO | H | 3.0 |
| CH₃O | CH₃ | 3.0 |
| CH₃CO.O | CH₃CO | 1.0 |
| C₂H₅CO.O | C₂H₅CO | 0.3 |
| H | CH₃CO | 1.0 |
| H | HCO | 0.5 |

| | |
|---|---|
| | (structure: benzene with R³, NH-CH(CCl₃)-O-CH₂) |
| R³ | ED₅₀ |
| H | 1.0 |
| CH₃ | 3.0 |
| NO₂ | 0.5 |
| I | 1.0 |
| CH₃O | 0.3 |
| CN | 0.3 |

EXAMPLE 13

2-Amino-3-methylbenzyl alcohol (1.7 g.) and anhydrous chloral (2.4 ml.) were mixed for 10 minutes with external ice-cooling, and the mixture was left to stand for ½ hour. The mixture was then chromatographed on silica, and elution with diethyl ether/petroleum ether (b.p. 60°–80° C.), 7:3 by volume, gave 1,2-dihydro-8-methyl-2-trichloromethyl-4$\underline{H}$-benzo[d]-[1,3]-oxazine, which was crystallised from aqueous ethanol, m.p. 69°–70° C.

The process described above was repeated, using the appropriate o-aminobenzyl alcohol as starting material, to give the following analogous products:

(a) 6-chloro-1,2-dihydro-2-trichloromethyl-4$\underline{H}$-benzo[d]-[1,3]-oxazine, m.p. 68°–70° C. In this case, the reaction was completed by heating on a steam bath for 2 minutes, and the chromatography solvent was ether/petrol, 8:2 by volume.

The 2-amino-5-chlorobenzyl alcohol used as the starting material in the preparation of this compound was obtained from 5-chloro-2-nitrobenzyl alcohol by the general process described in the last paragraph of Example 11(d), but using 10% palladium-on-charcoal instead of Adams' platinum oxide catalyst;

(b) methyl 1,2-dihydro-2-trichloromethyl-4$\underline{H}$-benzo[d]-[1,3]-oxazine-4-carboxylate, crystallised from cyclohexane, m.p. 114°–115° C. In this case, the reaction was completed by warming the reactants briefly on a steam bath, and the chromatography solvent was ether/petrol, 6:4 by volume.

The methyl o-aminomandelate (methyl α-2-aminophenylglycolate) used as the starting material in the above process may be obtained as follows:

o-Nitromandelic acid (5 g.) and thionyl chloride (50 ml.) were mixed, heated under reflux on a steam bath for 1 hour and cooled, then the excess of thionyl chloride was removed on a rotary evaporator at room temperature. The crude o-nitromandeloyl chloride thus obtained was carefully mixed with methanol (70 ml.), and after the initial vigorous reaction had subsided, the mixture was heated under reflux on a steam bath for 1 hour, cooled, and the solvent evaporated under reduced pressure. The oil thus obtained was chromatographed on silica, and elution with diethyl ether/petroleum ether (b.p. 60°–80° C.), 6:4 by volume yielded methyl o-nitromandelate. The methyl o-nitromandelate thus obtained was reduced by the general process described under (a) above to give the required starting material;

(c) ethyl 1,2-dihydro-2-trichloromethyl-4$\underline{H}$-benzo[d]-[1,3]oxazine-4-carboxylate, crystallised from cyclohexane, m.p. 127°–128° C. In this case, the reaction was completed by warming the reactants briefly on a steam bath, diluting the product with water and extracting with ether, drying the ether extract and evaporating the solvent prior to chromatography. The product was eluted from silica chromatography with ether/petrol, 8:2 by volume.

The ethyl o-aminomandelate used as the starting material in the above process was obtained by the sequence of reactions described in the latter part of (b) above, but reacting the o-nitromandeloyl chloride with ethanol in place of methanol;

(d) butyl 1,2-dihydro-2-trichloromethyl-4$\underline{H}$-benzo[d]-[1,3]-oxazine-4-carboxylate, crystallised from cyclohexane, m.p. 110°–111° C. In this case, the reaction was completed by warming the reactants briefly on a steam bath, and the chromatography solvent was ether/petrol, 6:4 by volume.

The butyl o-nitromandelate used as the starting material in the above process was prepared by the sequence of reactions described in the latter part of (b) above, but using n-butanol in place of methanol;

(e) N-phenyl 1,2-dihydro-2-trichloromethyl-4$\underline{H}$-benzo[d]-[1,3]-oxazine-4-carboxamide, m.p. 139°–140° C.

The N-phenyl o-nitromandelamide used as the starting material in the above process was obtained by the sequence of reactions described in the latter part of (b) above, but using aniline in place of methanol.

EXAMPLE 14

Methyl 4-amino-3-hydroxymethylbenzoate (1 g.) and anhydrous chloral (1 ml.) were mixed together, initially with external ice-cooling, and then on a steam bath for 5 minutes. The product was dissolved in ethyl acetate (100 ml.) and the solution was washed with water (50 ml.), then dried. The solvent was evaporated, and the residue was crystallized from a mixture of ethyl acetate and petroleum ether (b.p. 60°–80 C.) to give methyl 1,2-dihydro-2-trichloromethyl-4H-benzo[d]-[1,3]-oxazine-6-carboxylate, m.p. 178°–179° C.

The methyl 4-amino-3-hydroxymethylbenzoate used as the starting material in the above process was obtained by reducing dimethyl 4-amino-iso-phthalate (5 g.) in ether (100 ml., dried over sodium) with lithium aluminium hydride (2 g.). The mixture was stirred at room temperature for 3.5 hours, then water (50 ml.) was added cautiously. The organic phase was separated and dried, the solvent was evaporated, and the residue was purified by silica gel chromatography, eluting with diethyl ether/petroleum ether (b.p. 60°–80° C.), 4:1 by volume. The product thus obtained was crystallised from ethyl acetate/petroleum ether (b.p. 60°–80° C.) to give the required starting material, m.p. 116°–117° C.

The process described above was repeated, using the appropriate o-aminobenzyl alcohol as starting material, to give the following analogous products:
(a) 1,2-dihydro-2-trichloromethyl-4H-benzo-[d]-[1,3]-oxazine-4-carboxylic acid, crystallised from aqueous acetic acid, m.p. 141°–143° C. In this case, the reaction product was dissolved in diethyl ether instead of ethyl acetate.
(b) propyl 1,2-dihydro-2-trichloromethyl-4H-benzo[d]-[1,3]-oxazine-4-carboxylate, crystallised from cyclohexane, m.p. 115°–116° C. In this case, the reaction product was simply extracted with cyclohexane, and the solution was treated with decolourising carbon before being allowed to crystallise.

The propyl o-aminomandelate used as the starting material in the above process may be obtained as follows:

o-Nitromandelic acid (12 g.) and thionyl chloride (75 ml.) were heated under reflux on a steam bath for 1 hour. The mixture was then cooled, the excess of thionyl chloride was evaporated under reduced pressure, and the residue was mixed with propanol, and heated under reflux on a steam bath for 1 hour. The excess of propanol was evaporated and the residue was purified by chromatography on silica, eluting with diethyl ether/petroleum ether (b.p. 60°–80° C.), 7:3 by volume, to give propyl o-nitromandelate. The propyl o-nitromandelate was then hydrogenated by the general process described in the latter part of Example 13(a) to give the required starting material.

(c) isopropyl 1,2-dihydro-2-trichloromethyl-4H-benZo[d]-[1,3]-oxazine-4-carboxylate, crystallised from cyclohexane as described in (b) above, m.p. 141°–142° C.

The isopropyl o-aminomandelate used as starting material in the above process was obtained by the sequence of reactions described in the latter part of (b) above, but using isopropanol in place of propanol.

Example 15

5-Acetoxy-2-aminobenzyl alcohol (8.8 g.) was dissolved in dry diethyl ether (150 ml.), anhydrous chloral (9.6 ml.) was added with stirring over 5 minutes, and the mixture was stirred overnight at room temperature. The solvent was evaporated, and the residue crystallised on stirring with a mixture of methanol (50 ml.) and water (25 ml.) to give 6-acetoxy-1,2-dihydro-2-trichloromethyl-4H-benzo[d]-[1,3]-oxazine, m.p. 155°–157° C.

The 5-acetoxy-2-aminobenzyl alcohol used as the starting material in the above process was obtained as follows:

A mixture of 5-hydroxy-2-nitrobenzaldehyde (4 g.) and acetic anhydride (10 ml.) was heated on a steam bath for 1 hour, then poured into water (100 ml.) and extracted with diethyl ether (3×50 ml.). The extracts were combined and dried, and the solvent was evaporated. The residue of 5-acetoxy-2-nitrobenzaldehyde was dissolved in absolute ethanol (100 ml.), and stirred and ice-cooled while sodium borohydride (1.5 g.) was added in portions. The reaction mixture was stirred at room temperature for 1 hour, then water (100 ml.) was added, and the mixture was extracted with ether (3×70 ml.). The extracts were combined and dried, and the solvent was evaporated to give 5-acetoxy-2-nitrobenzyl alcohol, which was hydrogenated by the general process described in the latter part of Example 13(a) to give the required starting material.

EXAMPLE 16

3,4-Dihydro-2-trichloromethyl-2H-benzo[e]-[1,3]-oxazin-4-one (prepared as described in Example 3—5 g.) was suspended in ethanol (100 ml.), 63 ml. of a solution of sodium hydroxide (1.0 g.) in ethanol (83 ml.) was added, and the mixture was stirred for 15 minutes to obtain a clear solution. Iodomethane (5 ml.) was added, and the solution was boiled under reflux for 30 minutes. The solvents were evaporated, and the residue was dissolved in a mixture of toluene and ethyl acetate (7:3 by volume) and chromatographed on silica, eluting with the same solvent mixture. The first 100 ml. of eluate was collected, the solvent was evaporated and the residue crystallised on trituration with petroleum ether (b.p. 60°–80° C.) to give 3,4-dihydro-3-methyl-2-trichloromethylbenzo[e]-[1,3]-oxazin-4-one, m.p. 82°–84° C.

EXAMPLE 17

The process described in Example 3 was repeated, using the appropriate salicylamide as starting material, to give the following analogous products:
(a) 3,4-dihydro-4-oxo-2-trichloromethyl-2H-benzo[e]-[1,3]-oxazine-6,8-dicarboxylic acid, crystallised from ethanol, m.p. 305°–307° C. (with decomposition);
(b) 3,4-dihydro-6-hydroxyiminomethyl-2-trichloromethyl-2-H-benzo[e]-[1,3]-oxazin-4-one, crystallised from ethanol, m.p. 228°–230° C. (with decomposition).

The 5-(hydroxyiminomethyl)salicylamide used as the starting material in this process may be obtained as follows:

Methyl 5-(hydroxyiminomethyl)salicylate (16.0 g.) was added in one portion to a saturated solution of ammonia in methanol (1.6 l.). The solution so obtained was stirred at room temperature for 24 hours and then evaporated to dryness, and the residue was triturated with ethanol (200 ml.) to give the required starting material, m.p. 225°–227° C. (with decomposition);
(c) 3,4-dihydro-2-trichloromethyl-2H-benzo[e]-[1,3]-oxazine-6-carbaldehyde, m.p. 203°–206° C. In this case, the suspension obtained on pouring the reaction mixture onto ice was filtered off, washed, dried and crystallised from aqueous ethanol, 1:1 (200 ml.). The first material to crystallise was discarded, the mother liquors were evaporated to dryness and the residue was dissolved in ethyl acetate (250 ml.). The ethyl acetate solution was washed with N sodium hydroxide solution (100 ml.), then with water, and was dried, and evaporation of the solvent gave the required product.

The 5-formylsalicylamide used as the starting material in this process was obtained by hydrolysing 5-(hydroxyiminomethyl)salicyalmide (prepared as described in (b) above) with 5 N hydrochloric acid, and extracting the reaction mixture with ethyl acetate; m.p. 188°–190° C. (with decomposition) after crystallisation from ethanol;

(d) 6-acetamido-3,4-dihydro-2-trichloromethyl-2H-benzo[e]-[1,3]-oxazin-4-one, crystallised from ethanol, m.p. 228°–230° C. (with decomposition);

(e) 3,4-dihydro-6-tosylamino-2-trichloromethyl-2H-benzo[e]-[1,3]-oxazin-4-one, crystallised from ethanol, m.p. 278°–280° C. (with decomposition);

EXAMPLE 18

3,4-Dihydro-4-oxo-2-trichloromethyl-2H-benzo[e]-[1,3]-oxazine-6-carboxamide (prepared as described in Example 10—1.0 g.) and thionyl chloride (20 ml.) were heated together under reflux for 1 hour, cooled to room temperature, and drowned into ice-water (200 ml.). After stirring for 1 hour, the white suspension so formed was filtered off, washed with water, dried at 60° C. and extracted with toluene (3×200 ml.). The toluene extracts were combined, and the solvent was evaporated to give 3,4-dihydro-4-oxo-2-trichloromethyl-2H-benzo[e]-[1,3]-oxazine-6-carbonitrile, m.p. 212°–214° C.

EXAMPLE 19

5-Amino-N-(1-hydroxy-2,2,2-trichloroethyl)salicylamide (23.0 g.) and concentrated sulphuric acid (115 ml.) were heated on a steam bath for 1 hour, then poured onto ice (1 l.). The resulting mixture was stirred for 30 minutes and filtered. The filtrate was adjusted to pH 5 with 5 N sodium hydroxide solution and stirred for 30 minutes, and the precipitated product was filtered off, washed with water, and dried at 60° C. to give 6-amino-3,4-dihydro-2-trichloromethyl-2H-benzo[e]-[1,3]-oxazin-4-one, m.p. 172°–174° C.

The 5-amino-N-(1-hydroxy-2,2,2-trichloroethyl)-salicylamide used as starting material in this process may be obtained as follows:

5-Nitrosalicyalamide (10.0 g.) and anhydrous chloral (100 ml.) were heated together on a steam bath overnight, the solution was cooled, and the excess of chloral was evaporated under reduced pressure at 50° C. The oily residue was triturated with toluene (100 ml.) for 30 minutes, and the solid product was filtered off and crystallised from benzene to give N-(1-hydroxy-2,2,2-trichloroethyl)-5-nitrosalicyamide, m.p. 223°–225° C.

N-(1-hydroxy-2,2,2-trichloroethyl)-5-nitrosalicyalamide (69 g.) was stirred in glacial acetic acid (1380 ml.), and zinc dust (109 g.) was added in portions over 3 hours, at a temperature of 30°–37° C. The resulting suspension was filtered, the residue was washed with glacial acetic acid, and the combined filtrate and washings were evaporated under reduced pressure at 50° C. to a dark oil. The oil was mixed with 2 N hydrochloric acid, stirred for 30 minutes and filtered. The residue was washed with 2 N hydrochloric acid, and the filtrate and washings were combined and neutralised with 2 N sodium hydroxide. The neutralised mixture was stirred for 30 minutes and filtered. The solid product was washed with water, dried and extracted with ethyl acetate (3×1 l.). The extracts were then combined and evaporated to dryness to give the required starting material.

EXAMPLE 20

A suspension of 6-p-chlorobenzylideneamino-3,4-dihydro-2-trichloromethyl-2H-benzo[e]-[1,3]-oxazin-4-one (5.1 g.) in ethanol (3 l.) was heated to 50° C. to obtain a solution, and sodium borohydride (4.6 g.) was added over 30 minutes. The reaction mixture was then cooled, and the solvent was evaporated at 40° C. under reduced pressure. The residue was mixed with water (50 ml.), the pH was adjusted to 8 with 2 N hydrochloric acid, and after 15 minutes, the solid product was filtered off, washed with water and dried. This product was dissolved in diethyl ether (1 l.), and the solution was washed successively with water, 2 N hydrochloric acid, water, 2 N sodium hydroxide solution and water, and was then dried. Evaporation of the solvent gave 6-p-chlorobenzylamino-3,4-dihydro-2-tichloromethyl-2H-benzo[e]-[1,3]-oxazin-4-one, m.p. 156°–158° C.

The 6-p-chlorobenzylideneamino-3,4-dihydro-2-trichloromethyl-2H-benzo[e]-[1,3]-oxazin-4-one used as the starting material in this process may be obtained by mixing ethanolic solutions of 6-amino-3,4-dihydro-2-trichloromethyl-2H-benzo[e]-[1,3]-oxazin-4-one (obtained as described in Example 19—1 g. in 60 ml.) and p-chlorobenzaldehyde (0.5 g. in 15 ml.), heating the mixture for 10 minutes on a steam bath, and allowing the required product to crystallise from the solution on cooling; m.p. 246°–249° C.

EXAMPLE 21

A mixture of 3,4-dihydro-2-trichloromethyl-2H-benzo[e]-[1,3]-oxazin-4-one (10 g.—obtained as described in Example 3) and concentrated sulphuric acid (100 ml.) was heated on a steam bath for 18 hours, and drowned into ice (400 g.). The resulting solution was saturated with sodium chloride and extracted with ethyl acetae (4×100 ml.) The extracts were combined and dried, the solvent was evaporated, and the residue was crystallised from glacial acetic acid to give 3,4-dihydro-2-trichloromethyl-2H-benzo[e]-[1,3]-oxazine-6-sulphonic acid, m.p. > 260° C.

EXAMPLE 22

The process described in Example 1 was repeated, using 5-methoxycarbonylanthranilamide in place of anthranilamide, and including bis(2-methoxyethyl)ether (76 ml.) as a diluent, to give methyl 1,2-dihydro-4-oxo-2-trichloromethylquinazoline-6-carboxylate, m.p. 249° C. (with decomposition).

EXAMPLE 23

N-(1-hydroxy-2,2,2-trichloroethyl)-5-methoxycarbonylanthranilamide (5 g.) and concentrated sulphuric acid (100 ml.) were heated together on a steam bath for 15 minutes, cooled, and poured onto a minimum quantity of ice. The precipitate thus formed was filtered off, dried and dissolved in hot ethanol (300 ml.). The ethanol solution was concentrated to 20 ml. and the solid produced was filtered off and discarded. The filtrate was further concentrated to 10 ml. and the product thus obtained was filtered off, dried and crystallised from glacial acetic acid/water, 1:1, to give 1,2-dihydro-4-oxo-2-trichloromethylquinazoline-6-carboxylic acid, m.p. > 280° C.

The N-(1-hydroxy-2,2,2-trichloroethyl)-5-methoxycarbonylanthranilamide, used as starting material in the above process, may be obtained as follows:

5-Methoxycarbonyl-2-nitrobenzoic acid (70 g.) and thionyl chloride (350 ml.) were heated together on a steam bath for 5¼ hours, the reaction mixture was cooled, and the remaining thionyl chloride was evaporated under reduced pressure.

The residue was dissolved in toluene (700 ml.) and the solution was cooled in ice while ammonia was bubbled through for 1¾ hours. The solid product thus produced was filtered off, washed with toluene and then petroleum ether (b.p. 60°–80° C.), and was then stirred with water for 1 hour, filtered off and dried to give 5-methoxycarbonyl-2-nitrobenzamide.

5-Methoxycarbonyl-2-nitrobenzamide (28 g.) was dissolved in methanol (600 ml.), 10% palladium-on-charcoal catalyst (3 g.) was added, and the mixture was hydrogenated for 6 hours at about 35° C. The catalyst was filtered off, extracted with methanol (350 ml.) at reflux temperature under an atmosphere of nitrogen for 20 minutes, and filtered again. Both filtrates were evaporated to dryness, and the combined residues were crystallised from water (3 l.) to give 5-methoxycarbonylanthranilamide, m.p. 188°–193° C.

5-Methoxycarbonylanthranilamide (1.0 g.) anhydrous chloral (5 ml.) and bis(2-methoxyethyl) ether (20 ml.) were heated together on a steam bath for 20 minutes, then evaporated to dryness under reduced pressure. The residue solidified on stirring with diethyl ether, and it was filtered off and purified by chromatography on silica gel (250 g.). The column was eluted with a mixture of ethyl formate and toluene (7:3 by volume), and 50 ml. fractions were collected. Fractions 10 to 13 were combined and evaporated to dryness, and the residue solidified on stirring with petroleum ether (b.p. 60°–80° C.) to give the required starting material, N-(1-hydroxy-2,2,2-trichloroethyl)-5-methoxycarbonylanthranilamide, m.p. 93° C. (with decomposition).

EXAMPLE 24

1,2-dihydro-4-oxo-2-trichloromethylquinazoline-6-carboxylic acid (0.5 g.), ethanol (6 ml.) and concentrated sulphuric acid (3 ml.) were heated together under reflux on a steam bath for 1.5 hours. The reaction mixture was filtered, and the filtrate was poured onto a minimum quantity of ice. The precipitate thus produced was filtered off, washed with water and dried, to give ethyl 1,2-dihydro-4-oxo-2-trichloromethylquinazoline-6-carboxylate, m.p. 243°–244° C.

EXAMPLE 25

1,2-Dihydro-2-trichloromethylquinazolin-4-one (3.0 g.), acetic anhydride (25 ml.) and a few drops of concentrated sulphuric acid were heated together on a steam bath for 1½ hours, and the resulting solution was cooled and poured into water (250 ml.). The mixture was stirred for 2 hours and then filtered, and the residue was filtered off, washed with water, dried and crystallised from ethanol to give 1,3-diacetyl-1,2-dihydro-2-trichloromethylquinazolin-4-one, m.p. 152°–154° C.

EXAMPLE 26

The test of methane inhibition described in Example 12 was repeated for various other compounds, to give the results shown below. The results are expressed as the percentage inhibition of methane production caused by 1 μg./ml. of a test compound, except for those compounds indicated by *, for which 3 μg./ml. was used.

| $R^1$ | $R^3$ | $R^5$ | % Methane Inhibition at 1μg./ml. |
|---|---|---|---|
| H | CN | H | 87* |
| COOH | COOH | H | 38 |
| H | CHO | H | 47 |
| H | HO . N:CH | H | 41 |
| H | $NH_2$ | H | 98 |
| H | $CH_3CONH$ | H | 96 |
| H | p-$CH_3$ . $C_6H_4SO_2NH$ | H | 94 |
| H | p-Cl . $C_6H_4$ . $CH_2NH$ | H | 86* |
| H | $SO_3H$ | H | 11 |
| H | H | $CH_3$ | 100 |

| $R^1$ | $R^3$ | $R^{11}$ | % Methane inhibition at 1μg./ml. |
|---|---|---|---|
| $CH_3$ | H | H | 100 |
| H | Cl | H | 100 |
| H | $CH_3O$ . CO | H | 100 |
| H | $CH_3CO$ . O | H | 30 |
| H | H | COOH | 14 |
| H | H | $CH_3O$ . CO | 46 |
| H | H | $C_2H_5O$ . CO | 24 |
| H | H | n-$C_3H_7O$ . CO | 31 |
| H | H | i-$C_3H_7O$ . CO | 37 |
| H | H | n-$C_4H_9O$ . CO | 12 |
| H | H | $C_6H_5NH$ . CO | 57 |

| $R^3$ | $R^5$ | $R^6$ | % Methane inhibition at 1μg./ml. |
|---|---|---|---|
| H | $CH_3CO$ | $CH_3CO$ | 90 |
| COOH | H | H | 5* |
| $C_2H_5O$ . CO | H | H | 71* |

EXAMPLE 27

Premixes suitable for incorporation into ruminant feedstuffs may be manufactured by incorporating 20, 30, 40 or 50 g. of a heterocyclic trichloromethyl compound of the formula I in a standard ruminant feedstuff, so that the final weight is 500 g.

A suitable standard ruminant feedstuff for cattle may comprise, for example:

Rolled barley —85% by weight
Extacted soya bean meal —10%
Molasses —4%
Vitamin/minerals mixture —1% and a suitable standard ruminant feedstuff for sheep may comprise, for example:

Rolled barley—60% by weight

Wheat feed—15%
Maize germ meal—10%
Extracted soya bean meal—6%
Molasses—7.5%
Vitamin/minerals mixture 1.5%
but the individual components may be varied widely according to local feeding requirements and availability of feedstuff components.

EXAMPLE 28

A feedstuff suitable for direct feeding to cattle is obtained by intimately mixing 500 g. of a premix, obtained as described in Example 27, with 4.5 kg. of the standard cattle feedstuff described in Example 27, and then uniformly mixing the mixture so obtained with 995 kg. of the standard feedstuff, to give a supplemented feedstuff containing 20, 30, 40 or 50 g. of the heterocyclic trichloromethyl compound per tonnue of feedstuff, depending on the concentration of the compound in the premix.

EXAMPLE 29

A feedstuff suitable for direct feeding to sheep may be obtained by mixing 500 g. of a premix, obtained as described in Example 27 with 4.5 kg. of the standard sheep diet described in Example 27, and then further dispersing the mixture so obtained in 995 kg. of the feedstuff, to obtain a supplemented feedstuff containing 20, 30 or 40 g. of a heterocyclic trichloromethyl compound of the formula I per tonne of feedstuff, depending on the concentration of the compound in the premix.

What we claim is:

1. A heterocyclic trichloromethyl compound of the formula:

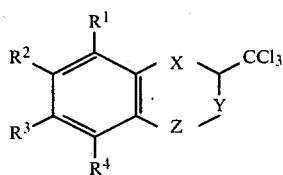

wherein:
X is an oxygen atom, Y is a radical of the formula —$NR^5$— wherein $R^5$ is a hydrogen atom, a 1-4C alkyl or alkanoyl radical or a phenyl radical which is optionally substituted by one or more halogen atoms, nitro radicals or 1-4C alkyl, alkoxy or halogenoalkyl radicals, Z is a carbonyl radical; and $R^1$, $R^2$, $R^3$ and $R^4$, which may be the same or different, are each a hydrogen or halogen atom, an cyano, formyl, hydroxy, hydroxyiminomethyl, nitro or sulfo radical, a carboxy radical or an alkali metal, alkaline earth metal or ammonium salt thereof, or a radical of the formula $R^7$, $OR^7$, $O.CH_2R^{10}$, $CO.OR^7$, $O.COR^7$, $O.COR^{10}$, $CO.NR^8R^9$, $NH.SO_2R^{10}$, $NR^8R^9$, $NR^8.COR^9$, $NH.CH_2R^{10}$, $SO_2.NR^8R^9$ or $SO_2.OR^7$ wherein $R^7$ is a 1-4C alkyl radical, $R^8$ and $R^9$, which may be the same or different, are each a hydrogen atom or a 1-4C alkyl radical and $R^{10}$ is a phenyl radical optionally substituted as defined above for $R^5$; but excluding those compounds wherein:
(i) X is an oxygen atom, Y is an imino radical and $R^1$, $R^2$, $R^3$ and $R^4$ are all hydrogen atoms; or
(ii) X is an oxygen atom, Y is an imino radical and either $R^2$ and $R^4$ are hydrogen atoms and $R^1$ and $R^3$ are chlorine atoms, or $R^3$ is an acetamido radical and $R^1$, $R^2$ and $R^4$ are hydrogen atoms; or
(iii) X is an oxygen atom, Y is an acetylimino radical, $R^3$ is an acetamido radical and $R^1$, $R^2$ and $R^4$ are all hydrogen atoms.

2. A heterocyclic trichloromethyl compound as claimed in claim 1 wherein $R^1$, $R^2$, $R^3$ and $R^4$, which may be the same or different, are each a hydrogen, chloride, bromine or iodine atom, or a cyano, formyl, hydroxy, hydroxyiminomethyl, nitro, sulfo, carboxy, methyl, ethyl, propyl, isopropyl, butyl, isobutyl, s-butyl, t-butyl, methoxy, ethoxy, propoxy, isopropoxy, butoxy, isobutoxy, s-butoxy, t-butoxy, benzyloxy, chlorobenzyloxy, methylbenzoyloxy, methoxycarbonyl, ethoxycarbonyl, propoxycarbonyl, butoxycarbonyl, isobutoxycarbonyl, s-butoxycarbonyl, t-butoxycarbonyl, acetoxy, propionyloxy, butyryloxy, isobutyryloxy, benzoyloxy, chlorobenzoyloxy, methylbenzoyloxy, carbamoyl, methylcarbamoyl, dimethylcarbamoyl, ethylcarbamoyl, diethylcarbamoyl, propylcarbamoyl, dipropylcarbamoyl, isopropylcarbamoyl, butylcarbamoyl, isobutylcarbamoyl, s-butylcarbamoyl, t-butylcarbamoyl, ethylmethylcarbamoyl, amino, methylamino, dimethylamino, ethylamino, diethylamino, propylamino, dipropylamino, isopropylamino, butylamino, isobutylamino, s-butylamino, t-butylamino, ethylmethylamino, acetamido, N-methylacetamido, N-ethylacetamido, N-propylacetamido, N-isopropylacetamido, N-butylacetamido, propionamido, N-methylpropionamido, N-ethylpropionamido, butyramido, N-methylbutyramido, N-ethylbutyramido, 2-methylpropionamido, N,2-dimethylpropionamido, benzylamino, chlorobenzylamino, bromobenzylamino, (methylbenzyl)amino, (ethylbenzyl)-amino, methoxybenzylamino, ethoxybenzylamino, (trichloromethylbenzyl)amino, sulfamoyl, methylsulfamoyl, dimethylsulfamoyl, ethylsulfamoyl, diethylsulfamoyl, propylsulfamoyl, dipropylsulfamoyl, isopropylsulfamoyl, butylsulfamoyl, isobutylsulfamoyl, s-butylsulfamoyl, t-butylsulfamoyl, ethylmethylsulfamoyl, methoxysulfonyl, ethoxysulfonyl, propoxysulfonyl, isopropoxysulfonyl, butoxysulfonyl, isobutoxysulfonyl, s-butoxysulphonyl or t-butoxysulfonyl radical; the radical —$NR^5$— an imino, methylimino, ethylimino, acetylimino or propionylimino radical; and Z is a carbonyl radical.

3. A heterocyclic trichloromethyl compound as claimed in claim 1 wherein $R^1$, $R^2$, $R^3$ and $R^4$ which may be the same or different are each a hydrogen, chlorine, bromine or iodine atom, or a cyano, formyl, hydroxy, hydroxyiminomethyl, nitro, sulfo, carboxy, methyl, methoxy, butoxy, benzyloxy, methoxycarbonyl, ethoxycarbonyl, butoxycarbonyl, acetoxy, propionyloxy, p-chlorobenzoyloxy, carbamoyl, diethylcarbamoyl, dipropylcarbamoyl, amino, acetamido, p-chlorobenzylamino or tosylamino radical; the radical —$NR^5$— is an amino, methylimino, formylimino, acetylimino or propionylimino radical, and Z is a carbonyl radical.

4. A heterocyclic trichloromethyl compound 3,4-dihydro-6-hydroxy-2-trichloromethyl-2H-benzo[e]-[1,3]-oxazin-4-one, 3,4-dihydro-4-oxo-2-trichloromethyl-2H-benzo[e]-[1,3]-oxazine-6-carboxylic acid, 6-acetoxy-3,4-dihydro-2-trichloromethyl-2H-benzo-[e]-[1,3]-oxazin-4-one.

5. A compound according to claim 1 wherein at least one of $R^1$-$R^4$ is carboxy or salt thereof or a radical of the formula $COOR^7$, $OCOR^7$ or $OCOR^{10}$.

6. A heterocyclic trichloromethyl compound according to claim 1, said compound being 3,4-dihydro-4-oxo-2-trichloromethyl-2H-benzo[e]-[1,3]-oxazine-6-carboxylic acid.

7. A method for reducing ruminal methane production and/or for increasing the proportion of propionic acid in the ruminal fluid, in domesticated ruminant animals, which comprises orally administering to the animals an effective amount of a heterocyclic trichloromethyl compound of the formula I wherein $R^1$, $R^2$, $R^3$, $R^4$, X, Y and Z have any of the meanings defined in claim 1.

8. A composition for reducing ruminal methane production and/or for increasing the proportion of propionic acid in the ruminal fluid, in domesticated ruminant animals, which comprises an effective amount of a heterocyclic trichloromethyl compound of the formula I wherein $R^1$, $R^2$, $R^3$, $R^4$, X, Y and Z have any of the meanings defined in claim 1, together with a solid or liquid edible, non-toxic diluent or carrier.

9. A composition as claimed in claim 8 which is in the form of a supplemented feedstuff, for direct feeding to animals, containing from 3 p.p.m. to 3,000 p.p.m. of a heterocyclic trichloromethyl compound as defined in claim 8 in admixture with a conventional ruminant feedstuff.

10. A composition as claimed in claim 8 which is in the form of a concentrated premix, for dilution with a conventional ruminant feedstuff to produce a supplemented feedstuff suitable for direct feeding, containing from 0.3% w/w to 50% w/w of a heterocyclic trichloromethyl compound as defined in claim 9 in admixture with either a conventional, nutritionally balanced ruminant feedstuff, an inert solid diluent of no nutritional value, starch or lactose.

* * * * *